United States Patent
Wood

(10) Patent No.: US 6,780,272 B2
(45) Date of Patent: Aug. 24, 2004

(54) METHOD FOR PRODUCING WEB FOR USE IN MAKING SHAPED ELASTIC EARS DISPOSABLE ABSORBENT ARTICLE DIAPERS

(75) Inventor: Leigh E. Wood, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 281 days.

(21) Appl. No.: 09/954,366

(22) Filed: Sep. 17, 2001

(65) Prior Publication Data

US 2003/0051804 A1 Mar. 20, 2003

(51) Int. Cl.$^7$ .......................... B32B 31/08; B32B 31/18
(52) U.S. Cl. ........................ 156/250; 156/265; 156/271
(58) Field of Search ................................ 156/160, 250, 156/253, 256, 259, 260, 264–265, 269, 271, 290, 291, 226, 227, 164; 83/27, 436.6; 604/358

(56) References Cited

U.S. PATENT DOCUMENTS

| | | |
|---|---|---|
| 3,264,765 A | 8/1966 | Holden et al. |
| 3,276,944 A | 10/1966 | Levy |
| 3,338,992 A | 8/1967 | Kinney |
| 3,341,394 A | 9/1967 | Kinney |
| 3,502,538 A | 3/1970 | Peterson |
| 3,502,733 A | 3/1970 | Hartmann |
| 3,542,615 A | 11/1970 | Dobo et al. |
| 3,562,356 A | 2/1971 | Nyberg et al. |
| 3,692,618 A | 9/1972 | Dorschner et al. |
| 3,700,633 A | 10/1972 | Wahl et al. |
| 4,116,917 A | 9/1978 | Eckert |
| 4,156,673 A | 5/1979 | Eckert |
| 4,340,563 A | 7/1982 | Appel et al. |
| 4,381,781 A | 5/1983 | Sciaraffa et al. |
| 4,857,067 A | 8/1989 | Wood et al. |
| 4,965,122 A | 10/1990 | Morman |
| 4,981,747 A | 1/1991 | Morman |
| 5,114,781 A | 5/1992 | Morman |
| 5,116,662 A | 5/1992 | Morman |
| 5,156,973 A | 10/1992 | Shanbrom |
| 5,226,992 A | 7/1993 | Morman |
| 5,344,691 A | 9/1994 | Hanschen et al. |
| 5,354,507 A | 10/1994 | De Malde et al. |
| 5,399,219 A | 3/1995 | Roessler et al. |
| 5,462,708 A | 10/1995 | Swenson et al. |
| 5,501,675 A | 3/1996 | Erskine |
| 5,540,796 A * | 7/1996 | Fries .......................... 156/164 |
| 6,159,584 A | 12/2000 | Eaton et al. |
| 6,217,692 B1 * | 4/2001 | Kling ......................... 156/229 |

FOREIGN PATENT DOCUMENTS

WO    WO 96/10481    4/1996

* cited by examiner

Primary Examiner—Richard Crispino
Assistant Examiner—Sing P Chan
(74) Attorney, Agent, or Firm—Gary L. Griswold; Robert W. Sprague; William J. Bond

(57) ABSTRACT

There is provided a process for forming profiled elastic laminates suitable for forming profiled elastic ear portions. The process comprises the steps of providing a continuous length of at least one elastic web material having a first width and a continuous length of a first extensible nonelastic web having a second width. The extensible web is extensible in at least the width dimension. The at least one elastic web material and the first extensible nonelastic web are joined to form a first laminate. The first laminate is cut into at least two adjacent continuous lengths of at least two nested profiled laminates. The nested profiled laminates each have at least one profiled edge. Adjacent profiled edges of adjacent profiled laminates are substantial negatives of each other. The adjacent profiled laminates are then physically separated from each other. A continuous lengths of second nonelastic webs having a third width are joined to one or more of the profiled laminates to form at least one second continuous laminate. The second continuous laminate is collected in a roll and then further cut into sets of matched profiled elastic ear portions.

27 Claims, 11 Drawing Sheets

METHOD FOR PRODUCING WEB FOR USE IN MAKING SHAPED ELASTIC EARS DISPOSABLE ABSORBENT ARTICLE DIAPERS

BRIEF DESCRIPTION OF THE INVENTION

This invention relates to a method for manufacturing shaped elastic ear portion laminates from continuous webs of elastic and nonelastic material. The shaped elastic ear portion laminates are particularly suited for use in disposable absorbent articles such as diapers and adult incontinence articles.

Disposable absorbent articles that can be fitted to a wearer traditionally use fastening systems that have functional closure components such as hook and loop fasteners or pressure-sensitive adhesive tapes. These closure components are traditionally providing on or as small tabs placed at a side edge of the absorbent article. A complementary piece, that the closure element engages with, is generally also provided. This complementary element is often on a main body portion of the disposable garment. The tabs are often placed on so called ear portions, which are cut from an edge portion of the disposable absorbent article. This ear portion is often supplied with an elastic, such as described in U.S. Pat. Nos. 4,857,067; 5,156,973 and 4,381,781. This cutting out of the ear portion from a larger absorbent article chassis involves the creation of large amounts of trim which is costly and requires disposal.

This ear portion has also been provided as a separate element attached to a main chassis of the absorbent article, which ear portion is provided with all the functional elements required, e.g., generally elastic, closure elements and means to attach to the chassis. This separately applied ear portion eliminates waste creation on the absorbent article manufacturing line and allows modifications to an ear portion construction without the need for modifying the more complicated absorbent article line. An example of such an ear construction is disclosed in U.S. Pat. No. 6,159,584 (Eaton et al.). There however is still the need with these ear portion laminates to reduce the creation of scrap and provide a laminate that can be easily used on an absorbent article manufacturing line at high-speed assembly rates.

SUMMARY OF THE INVENTION

The invention is directed at a process for forming profiled elastic laminates suitable for forming profiled elastic ear portions from continuous length rolls.

Initially there is provided a continuous length of at least one elastic web material having a first width and a continuous length of a first extensible nonelastic web having a second width. The at least one elastic web material and the first extensible nonelastic web are laminated to form a first dimensionally stable laminate of an indefinite length in the machine direction. This first laminate is then continuously cut into at least two adjacent continuous lengths of at least two nested profiled laminates, which nested profiled laminates each have at least one profiled edge. The adjacent profiled edges of adjacent profiled laminates, cut from the first laminate, are generally substantial negatives of each other so that no trim needs to be removed between the adjacent profiled laminates when they are separated. These profiled laminates are also substantially continuous or of an indefinite length. The at least two adjacent profiled laminates are then separated from each other. A continuous length of at least one second nonelastic web having a third width is then provided. This at least one second nonelastic web is then laminated to at least one of the profiled laminates to form at least one second dimensionally stable continuous laminate. This second dimensionally stable continuous laminate can then be further provided with fastener elements and cut into individual profiled elastic ear portions for use on a disposable garment. The elastic region of the laminate can optionally be activated prior to, during or after the individual elastic ear portions are cut from the at least one second dimensionally stable web, or a web cut from the second dimensionally stable web.

DETAILED DESCRIPTION OF THE PREFERRED EMBODIMENT

Figure 1:
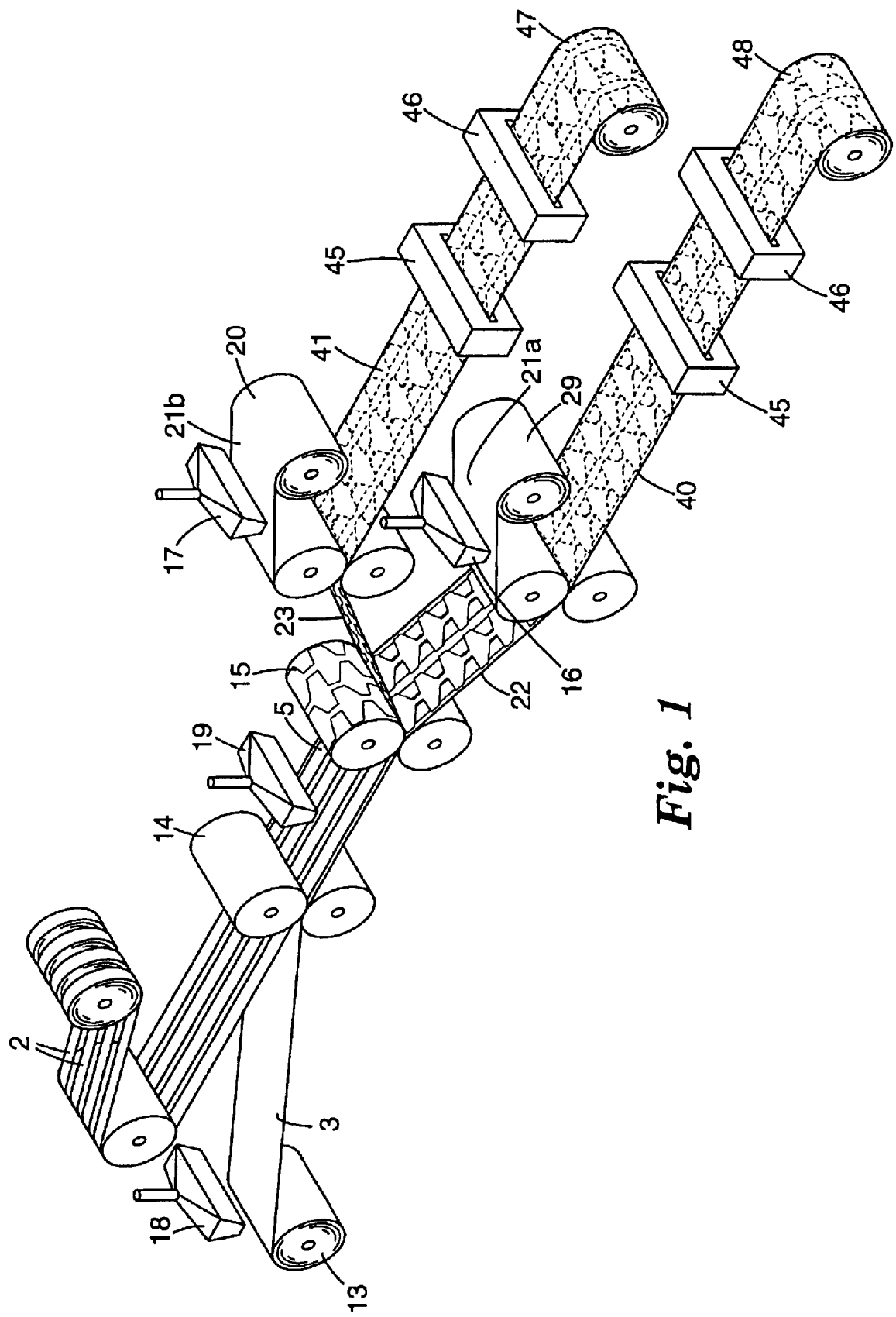
FIG. 1 is a perspective view of an apparatus and method according to a first embodiment of the present invention.

A first embodiment of the invention is shown in FIG. 1. There is provided a continuous length of at least one elastic web material 2 from a roll or the like. The elastic web can be any suitable flat elastic web including a film type elastic or nonwoven elastic. In a preferred embodiment, the elastic web material is an elastic film and preferably a coextruded elastic film, such as disclosed in U.S. Pat. Nos. 5,501,675; 5,462,708, 5,354,507 or 5,344,691, the substance of which are incorporated herein by reference. These references teach various forms of multilayer coextruded elastic laminates, with at least one elastic layer and either one or two relatively inelastic skin or outer layers. The inelastic layers can be stretched beyond an elastic limit of these layers (i.e., they are permanently deformed) and the laminate subsequently recovered in the direction opposite to the stretching direction by the relatively higher elastic recovery forces of the elastic layer. The inelastic layers provide a secure attachment surface to adhesively attach a nonwoven layer without fear of migration of the adhesive tackifying components into the elastic material.

The skin or outer layers are generally nontacky materials or blends formed of any semicrystalline or amorphous polymer(s) which are less elastomeric than the elastic layer, generally inelastic, and which will undergo relatively more permanent deformation than the core layer at the percentage that the elastic laminate is stretched.

The elastic web material is formed of a material, which exhibits elastomeric properties at ambient conditions. Elastomeric means that the material will substantially resume its original shape after being stretched. Preferably, the elastomer will sustain only small permanent set following deformation and relaxation, which set is preferably less than 30 percent and more preferably less than 20 percent of the original dimension after 50 to 500% stretch. The elastomeric material can be either pure elastomers or blends with an elastomeric phase or content that will still exhibit substantial elastomeric properties at room temperature. Suitable elastomeric thermoplastic polymers include block copolymers such as those know to those skilled in the art as A-B or A-B-A type block copolymers or the like. These block copolymers are described, for example, in U.S. Pat. Nos. 3,265,765; 3,562,356; 3,700,633; 4,116,917 and 4,156,673, the substance of which are incorporated herein by reference. Styrene/isoprene, butadiene or ethylene-butylene/styrene (SIS, SBS or SEBS) block copolymer are particularly useful. (Generally, there are two or more blocks, at least one A-block and at least one B-block, where the blocks can be arranged in any order including linear, radial, branched, or star block copolymers.) Other useful elastomeric compositions can include elastomeric polyurethanes, ethylene copolymers such as ethylene vinyl acetate, ethylene/propylene copolymer elastomers or ethylene/propylene/diene terpolymer elastomers. Blends of these elastomers with each other or with modifying non-elastomers are also contemplated.

The elastic web material 2 has a first width. Plural lengths of elastic webs are preferable provided from either a single roll, as shown, or multiple supply rolls or the like. A continuous length of a first extensible generally nonelastic web 3 having a second width is supplied, also preferably from a roll. The extensible nonelastic web is preferably a nonwoven web. The nonwoven web, generally is capable of extending by at least 30 percent of its original width dimension, preferably at least 75 percent where the preferred range of extensibility is from 50 to 400 percent most preferably from 75 to 400 percent The nonelastic extensible web can be continuously or intermittently attached to the elastic web or webs. If they are continuously attached, or intermittently attached while coplanar along either respective surfaces, the elastic web/nonelastic web laminate will generally need to be stretched to activate the elastic laminate. This is in order to overcome the tensile resistance of the extensible nonelastic web and/or skin layers for a coextruded elastic, as described above. This activation is generally accomplished by stretching by a variety of known techniques. The nonelastic web material can also be intermittently attached to the elastic webs where the nonelastic web has a dimension longer than the elastic web in the direction of intended elasticity for the elastic ear portion. For example the nonelastic web can be intermittently attached to an elastic web at linear attachment regions with arcuate portions of the nonelastic web projecting outward from adjacent linear attachment regions. Preferably however the nonelastic web is continuous and planar over at least a portion of its width dimension extending in the length or machine direction to provide for dimensional stability of the laminate in the machine direction. The length of the nonwoven web in the arcuate portions is greater than the length of the elastic web material between the same two adjacent attachment regions. The attachment regions could be linear, nonlinear or intermittent (e.g., point bond, segmented bond lines, circular bonds or the like) and/or randomly spaced and substantially parallel and still provide uniform elastic properties. Uniform elastic properties are also possible with point bonds or bond regions arranged in a uniform array or geometric pattern or with nonlinear bond lines that intersect in a uniform geometric pattern. By uniform geometric pattern it is meant that the amount of nonwoven material between, or within, a given bond pattern is substantially uniform across the length and width of the extensible portion. Nonuniform elastic properties could be provided by providing attachment regions that are nonparallel. For example, the attachment region spacing could vary in the cross direction of the extensible elastic ear portion providing an ear portion with differing degrees of elasticity along its width. For example, bond points or lines could be randomly spaced, converge, diverge, or increase in size and/or frequency. Also elastic properties can be varied by changing the amplitude or size of one or more of the arcuate portions either in the direction of extensibility or the width direction.

The extensible nonelastic web is preferably a nonwoven web having an initial yield tensile force of at least 100 gm/cm, preferably at least 300 gm/cm. Suitable processes for making the nonwoven web include, but are not limited to, airlaying, spunbond, spunlace, bonded melt blown webs and bonded carded web formation processes. Spunbond nonwoven webs are made by extruding a molten thermoplastic, as filaments from a series of fine die orifices in a spinneret. The diameter of the extruded filaments is rapidly reduced under tension by, for example, by noneductive or eductive fluid-drawing or other known spunbond mechanisms, such as described in U.S. Pat. No. 4,340,563 (Appel et al.); U.S. Pat. No. 3,692,618 (Dorschner et al.); U.S. Pat. Nos. 3,338,992 and 3,341,394 (Kinney); U.S. Pat. No. 3,276,944 (Levy); U.S. Pat. No. 3,502,538 (Peterson); U.S. Pat. No. 3,502,763 (Hartman) and U.S. Pat. No. 3,542, 615 (Dobo et al.). The spunbond web is preferably bonded (point or continuous bonding). The nonwoven web layer may also be made from bonded carded webs. Carded webs are made from separated staple fibers, which fibers are sent through a combing or carding unit which separates and aligns the staple fibers in the machine direction so as to form a generally machine direction oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Alternatively known meltblown webs or spunlace nonwoven webs or the like can be used to form the nonwoven webs of the invention extensible elastic ear portions. Meltblown webs are formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, meltblown webs must be further bonded such as by through air bonding, heat or ultrasonic bonding as described above.

A nonelastic web can also be made extensible by skip slitting of the nonelastic web in the intended extensible cross direction as is disclosed in PCT/WO96/10481. The slits are discontinuous and are generally cut on the web prior to the web being attached to the elastic. Although more difficult, it is also possible to create slits in the nonelastic web layer after the nonelastic web is laminated to the elastic web. At least a portion of the slits in the nonelastic web should be generally perpendicular (or have a substantial perpendicular vector) to the intended direction of extensibility or elasticity (the at least first direction) of the elastic web layer. By generally perpendicular it is meant that the angle between the longitudinal axis of the chosen slit or slits and the direction of extensibility is between 60 and 120 degrees. A sufficient number of the described slits are generally perpendicular such that the overall laminate is elastic. The provision of slits in two directions is advantageous when the elastic laminate is intended to be elastic in at least two different directions. With these nonelastic webs activation is not generally required.

An extensible nonwoven can also be a necked or reversibly necked nonwoven as described in U.S. Pat. Nos. 4,965, 122; 4,981,747; 5,114,781; 5,116,662 and 5,226,992. In these embodiments the nonwoven web is elongated or tensilized prior to attaching to the elastic web layers. With these nonelastic webs activation is generally not required.

Figure 2:
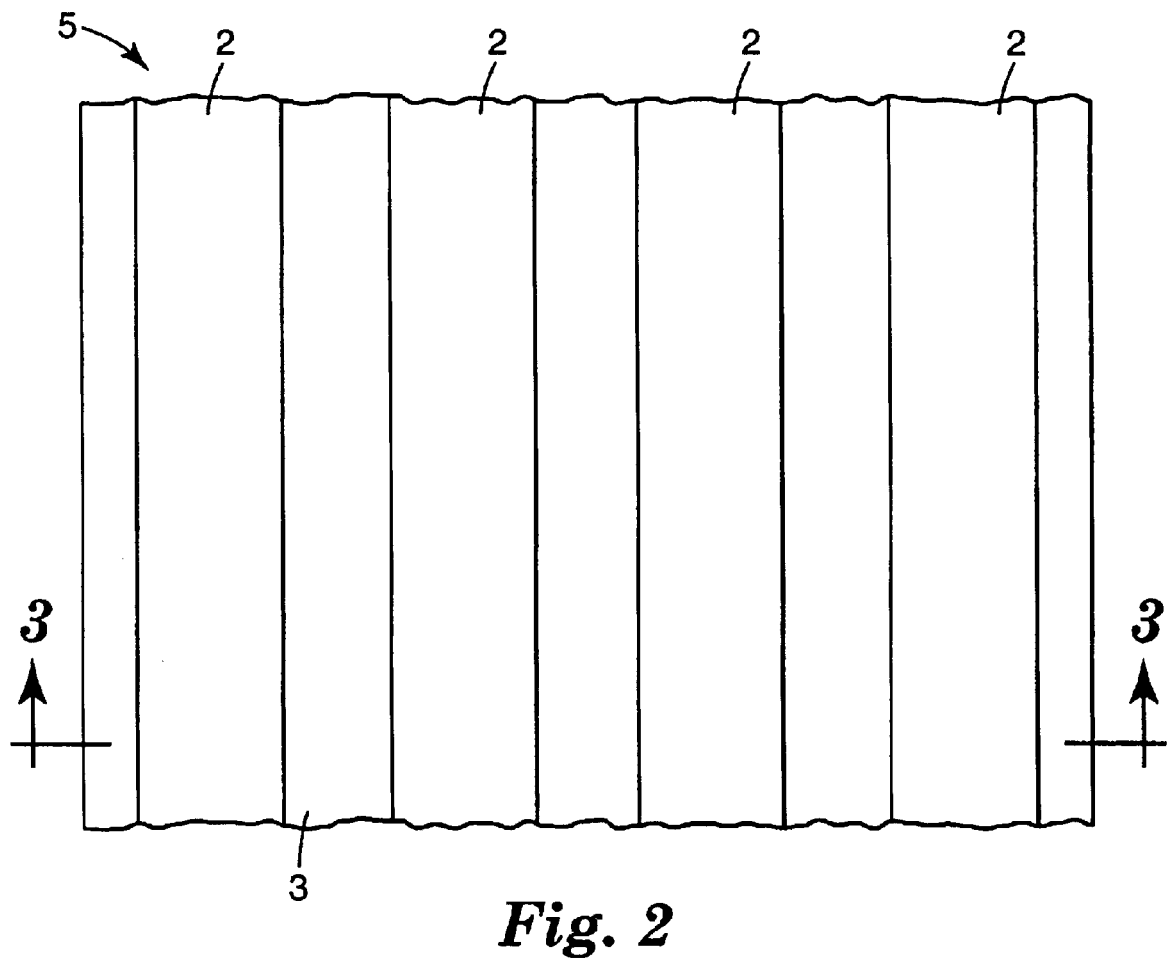
FIG. 2 is a cutaway top view of a first dimensionally stable laminate according to the first embodiment of FIG. 1.
Figure 3:
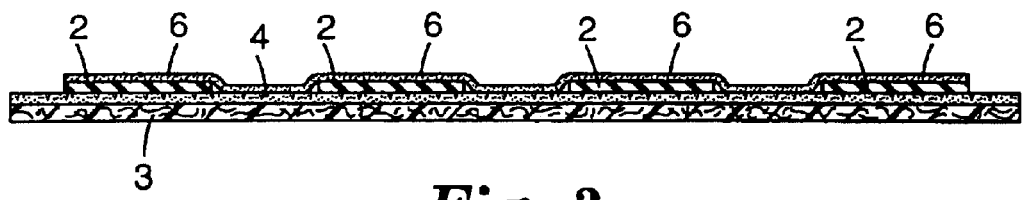
FIG. 3 is an end view of the FIG. 2 laminate.

The extensible nonelastic web 3 generally is wider than all the elastic web materials 2 combined so that multiple lengths of the elastic web can be attached to the nonwoven web 3 with space separating these ribbons or webs of elastic material. The at least one elastic web material and the first extensible nonelastic web are then laminated to form a first dimensionally stable laminate of an indefinite length in a nip 14. This lamination is preferably by use of an adhesive 4 supplied by an adhesive applicator 18. This can be a continuous adhesive application or an intermittent adhesive application. Thermal or ultrasonic bonding can also be used provided that the extensible web 3 does not lose its extensibility in the cross direction. Alternatively, an elastic film web can be directly extruded onto the extensible nonelastic web 3. A further layer of adhesive 6 can then be applied to the laminate 5 by adhesive applicator 19. This further layer of adhesive 6 allows the cutout versions of this laminate to be later joined to a second, preferably extensible nonwoven, nonelastic web. FIG. 2 is a top view of the first laminate 5 with FIG. 3 being an end view of the FIG. 2 laminate.

Figure 4:
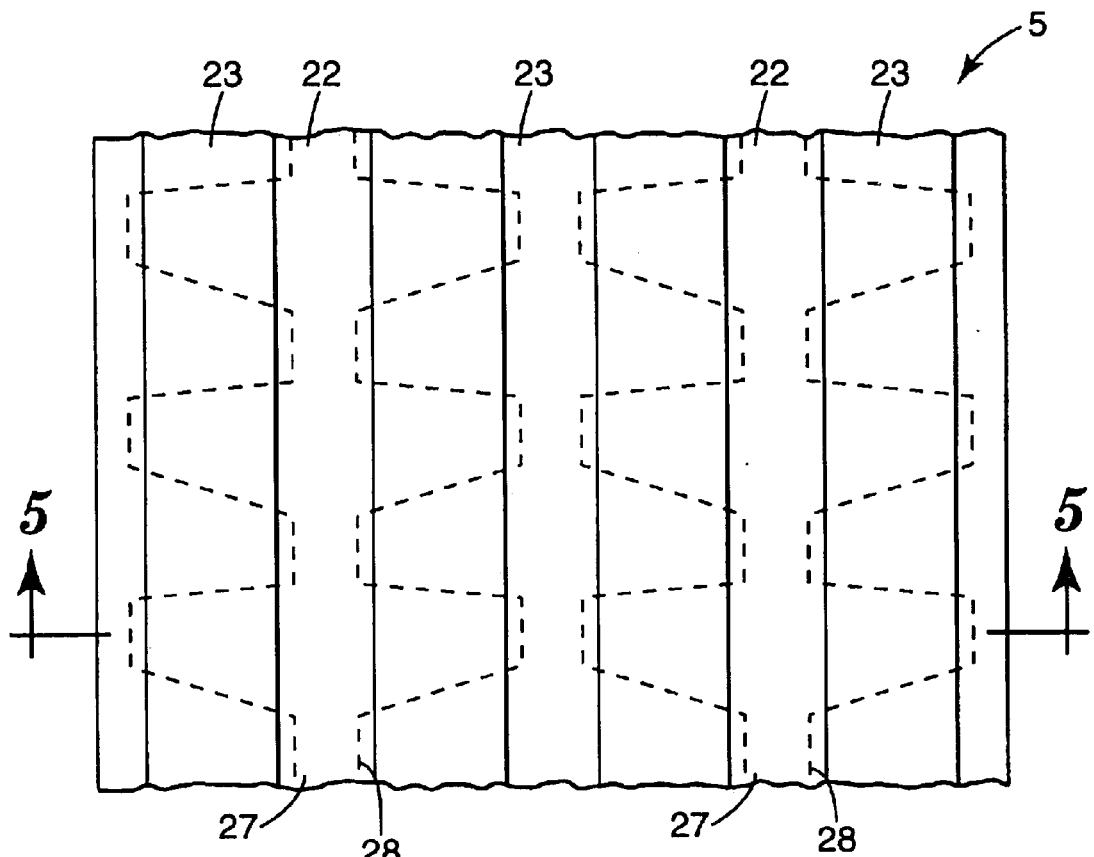
FIG. 4 is a top view of the FIG. 2 first laminate cut into a plurality of profiled laminates.
Figure 5:
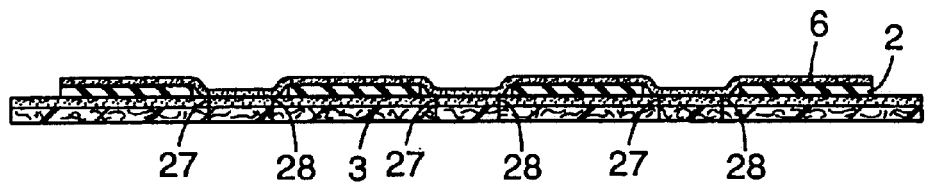
FIG. 5 is an end view of FIG. 4.
Figure 6:
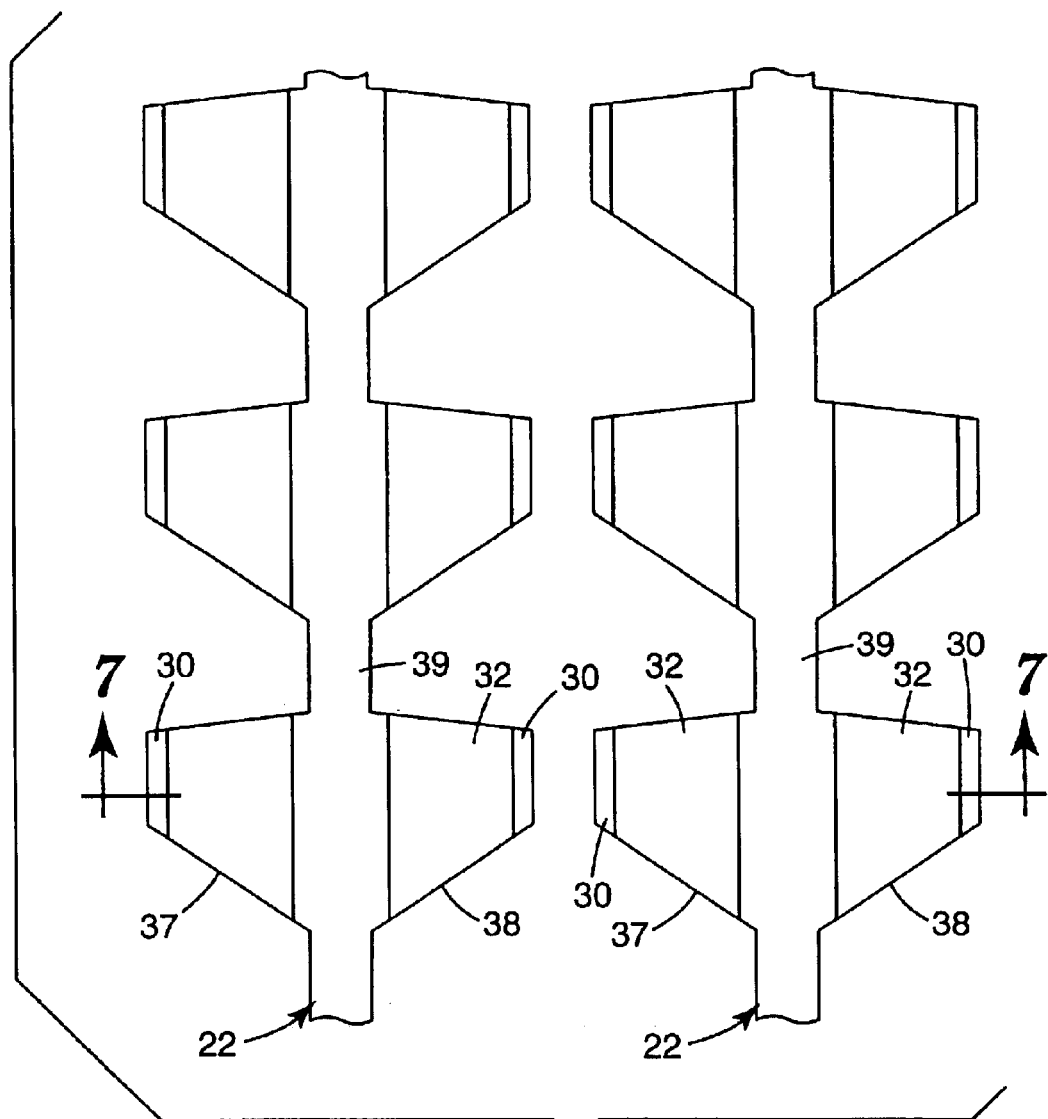
FIG. 6 is a top view of a first set of cut out profiled laminates that have been separated from the first laminate.
Figure 7:
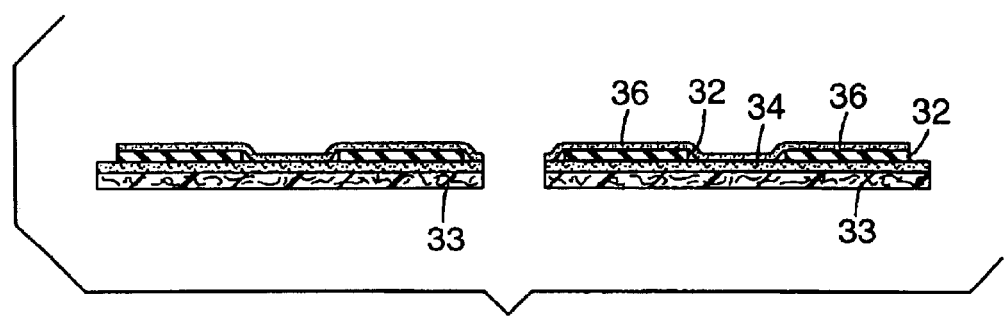
FIG. 7 is an end view of FIG. 6.
Figure 8:
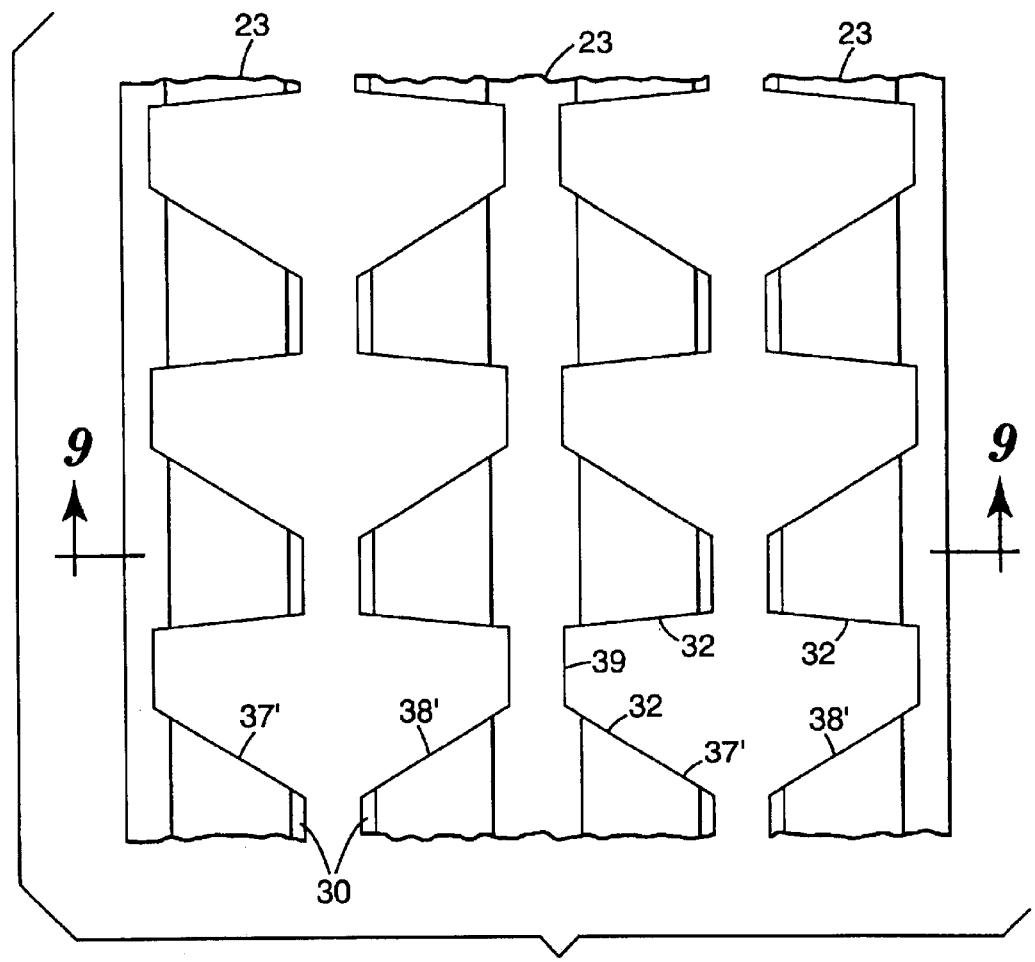
FIG. 8 is a top view of the adjacent second set of cut out profiled laminates that are a substantial mirror image of the FIG. 6 profiled laminates.
Figure 9:
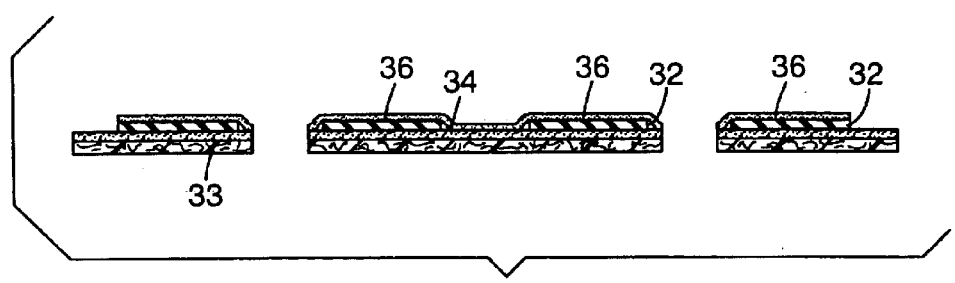
FIG. 9 is an end view of FIG. 8.

This first laminate 5 is then continuously cut into at least two adjacent continuous lengths of at least two nested profiled laminates 22 and 23 using a die cutter 15 or the like along cut lines 27 and 28, as shown in FIG. 4. Each nested profiled laminate will each have at least one profiled edge defined by the cut lines 27 and 28. The adjacent profiled edges (e.g., 37, 37' or 38, 38') of adjacent profiled laminates 22 and 23 cut from the first laminate 5, are generally substantial negatives, or mirror images, of each other so that no trim needs to be removed between the adjacent profiled laminates, as shown in FIGS. 4 and 5. Trim is excess material that would need to be removed and disposed of. These profiled laminates 22 and 23 are also substantially continuous, or with an indefinite length, in the machine direction. The at least two adjacent profiled laminates 22 and 23 are then separated from each other. If multiple profiled laminates of each of 22 and 23, as shown in FIGS. 6 and 8, are formed the alternate laminates are cut from the same laminate web 5. The first set of profiled laminates 22 are separated by spaces which spaces correspond to the other adjacent set of profiled laminate structures 23, and vice versa. The first set of profiled laminates 22, have opposing side edges 37 and 38 that are preferably mirror images of opposing side edges 37' and 38' of the second set of profiled laminates 23. The nonwoven layer 33, the elastic 32 and the adhesive layers 34 and 36, if provided, are also cut into the same profiled laminate structures as shown in FIGS. 7 and 9.

A continuous length of at least one second extensible nonelastic web 21 having a third width is the provided from a roll, 29 or 20. This second extensible web 21 can be identical to, or different than, the extensible web 3. Also this at least one second nonelastic web 21 (21a and 21b) is also preferably an extensible nonwoven web. This second extensible nonelastic web is laminated to the profiled laminates, 22 and/or 23, to form a second 41 and third 40 dimensionally stable continuous laminate. This laminating can be done using the adhesive layer 6 or optionally additional adhesive could be provided from adhesive applicators 16 and 17. The second dimensionally stable laminate 41 contains the first set of profiled laminates 22. These second set of profiled laminates 22 have inelastic regions 30 and 39. The elastic containing portions are separated by thin regions with no elastic. The elastic containing portions will eventually each form a series of one, or two, separate elastic ear portions which will be joined to a garment at preferably the inelastic regions 39. The opposite end with inelastic portion 30 will preferably contain a fastening element such as an adhesive layer, a mechanical fastener material such as a hook or a loop or alternatively a tab with a fastening element, can be provided at station 46.

The elastic can optionally be activated prior to or when the individual elastic elements are cut from the second dimensionally stable web, e.g., at station 45, by stretching a portion 32 of the second or third dimensionally stable web containing the elastic material 2. This stretching can be accomplished for example by intermeshing corrugating rolls, zone tentering devices or the like. The second or third dimensionally stable laminates can further be collected on a roll 47 and 48 for further cutting into smaller rolls of suitably matched profiled laminates as shown in FIGS. 14, 16 and 19, and or cut into individual profiled elastic elements for use on a disposable garment as shown in FIG. 18.

Figure 10:
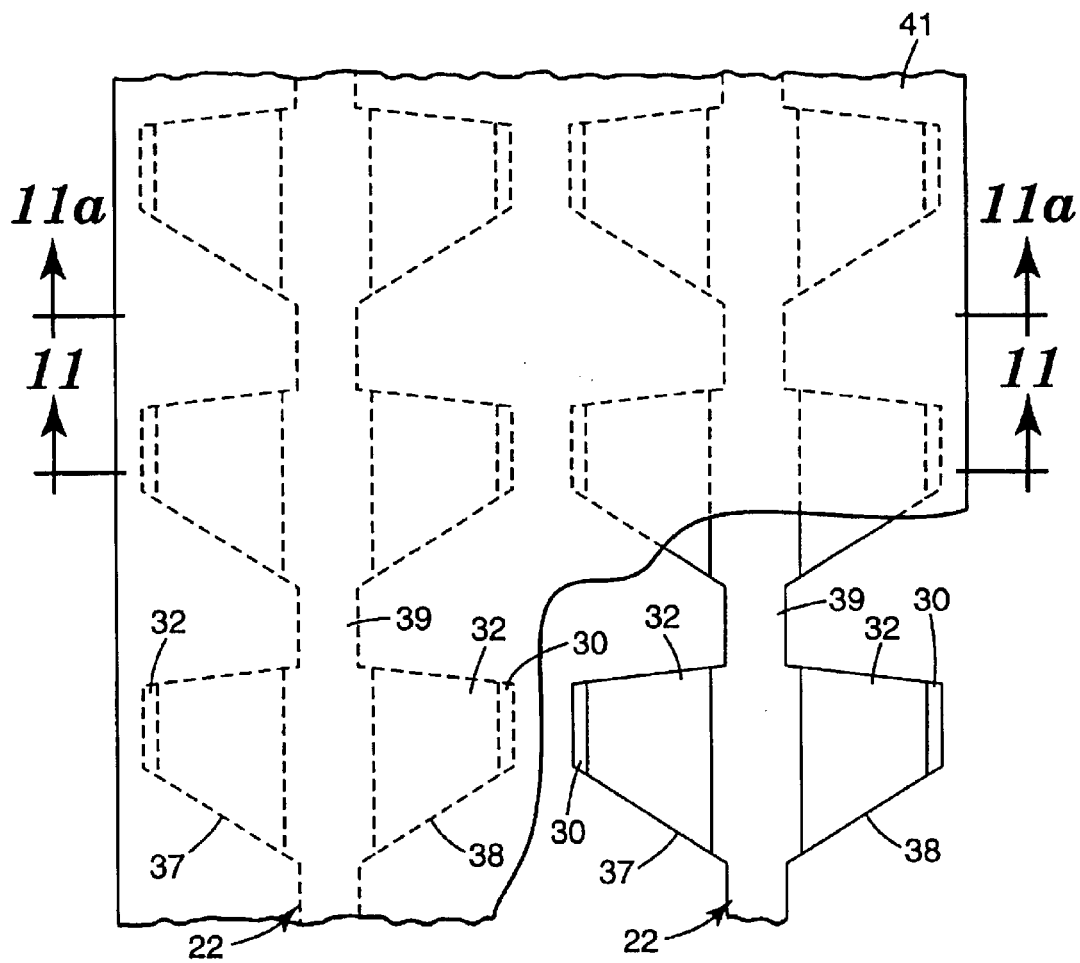
FIG. 10 is a cutaway top view of a second dimensionally stable laminate formed from the first set of profiled laminates.
Figure 11:
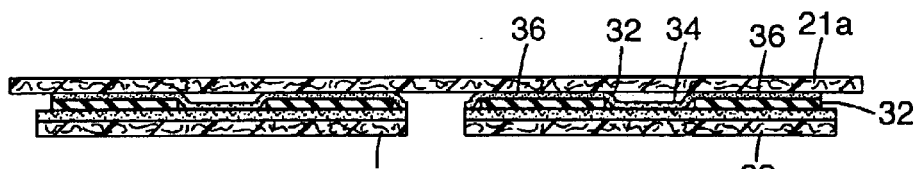
FIGS. 11 and 11a are end views of the FIG. 10 laminate.
Figure 11A:
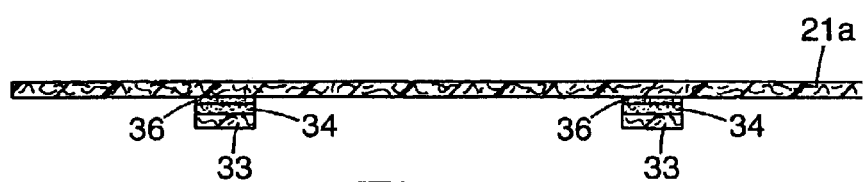
Figure 14:
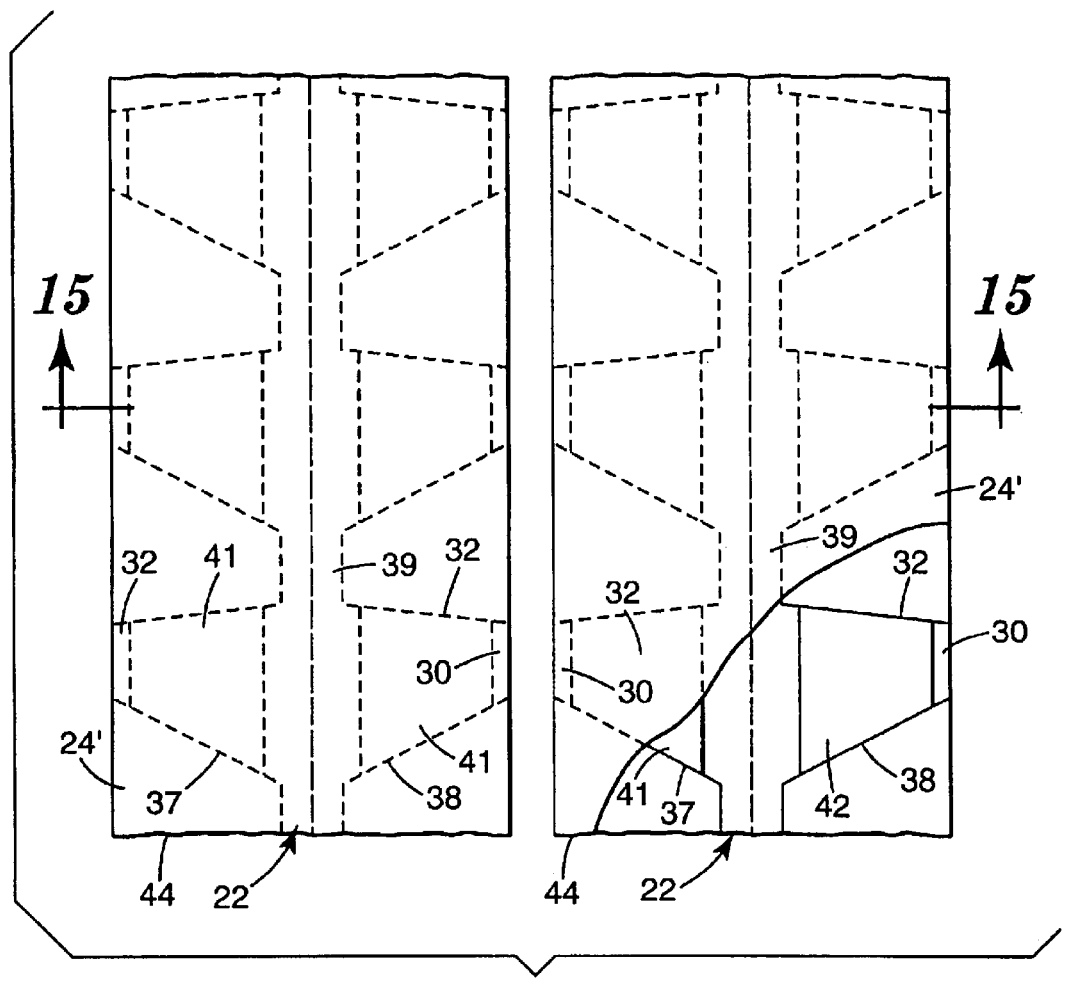
FIG. 14 is a top view of the FIG. 10 second dimensionally stable laminate further cut into a set of smaller second dimensionally stable laminates containing matched sets of ear portions for use on opposite sides of a disposable garment.
Figure 15:
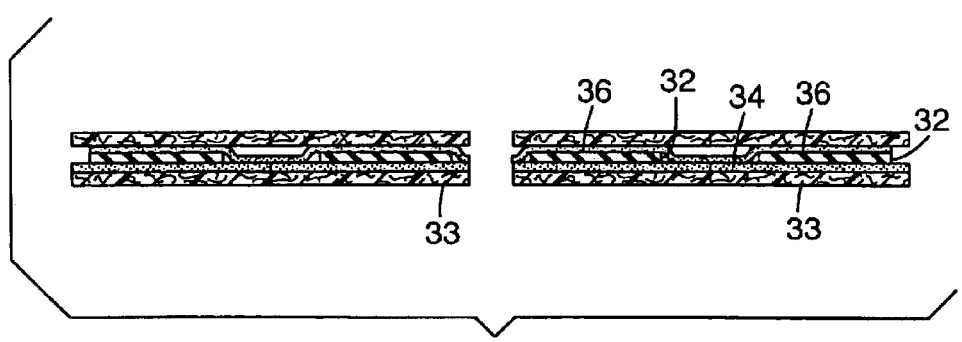
FIG. 15 is an end view of FIG. 14.

FIG. 14 is a top view of the FIG. 10 second dimensionally stable laminate further cut into a set of smaller second dimensionally stable laminates 44 containing matched sets of tabs 41 and 42 for use on opposite sides of a disposable garment. Each set of laminates 44 contain a series of matched sets of elastic ear portions 41 and 42 that be placed on opposite sides of a disposable garment or the like.

Figure 12:
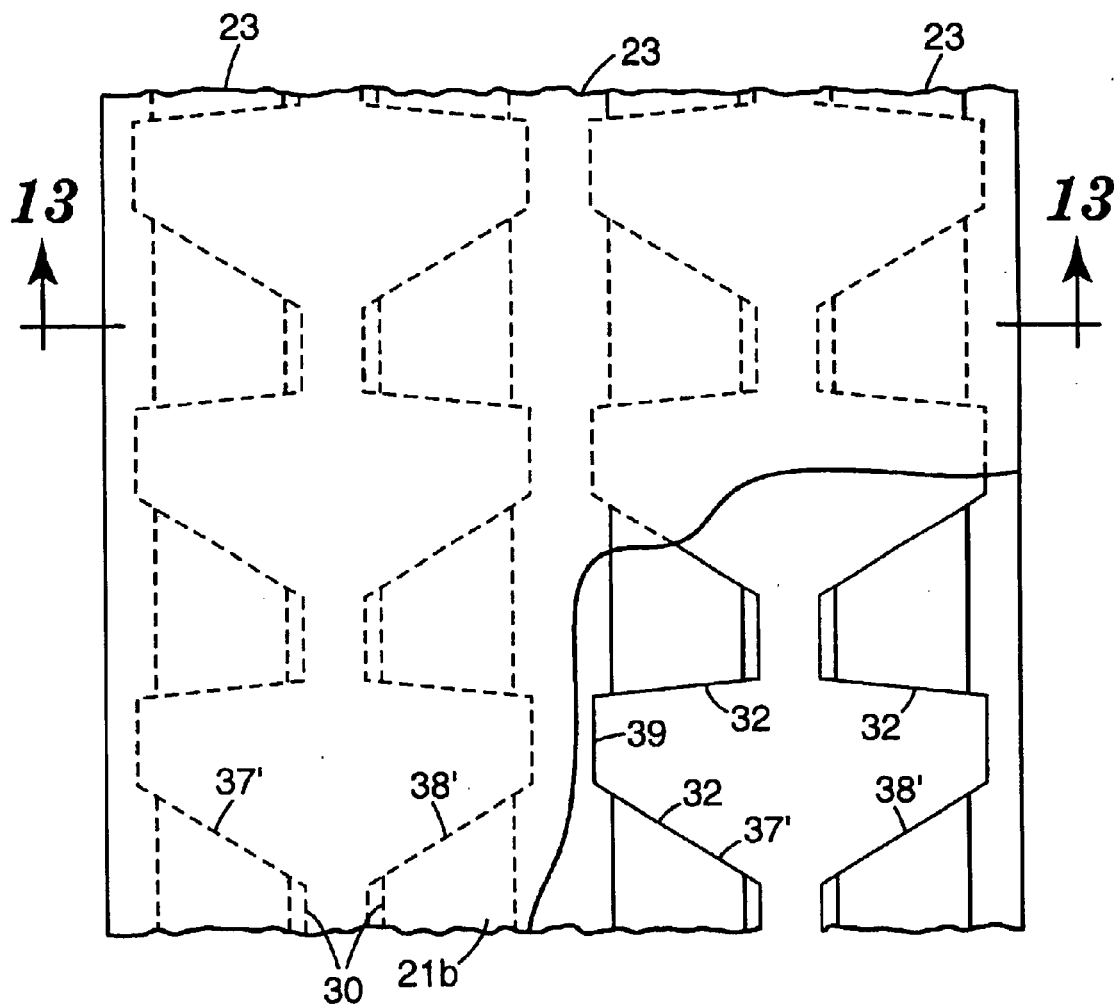
FIG. 12 is a cutaway top view of a third dimensionally stable laminate formed from the second set of profiled laminates of FIG. 8.
Figure 13:
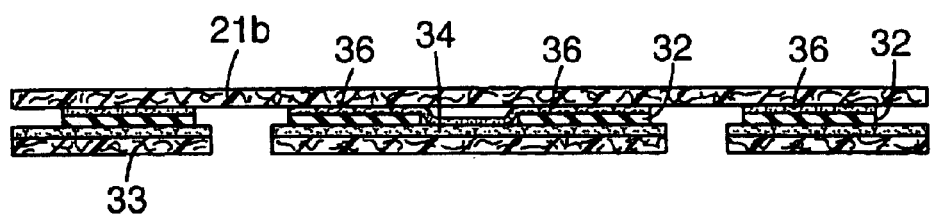
FIG. 13 is an end view of the FIG. 12 laminate.
Figure 16:
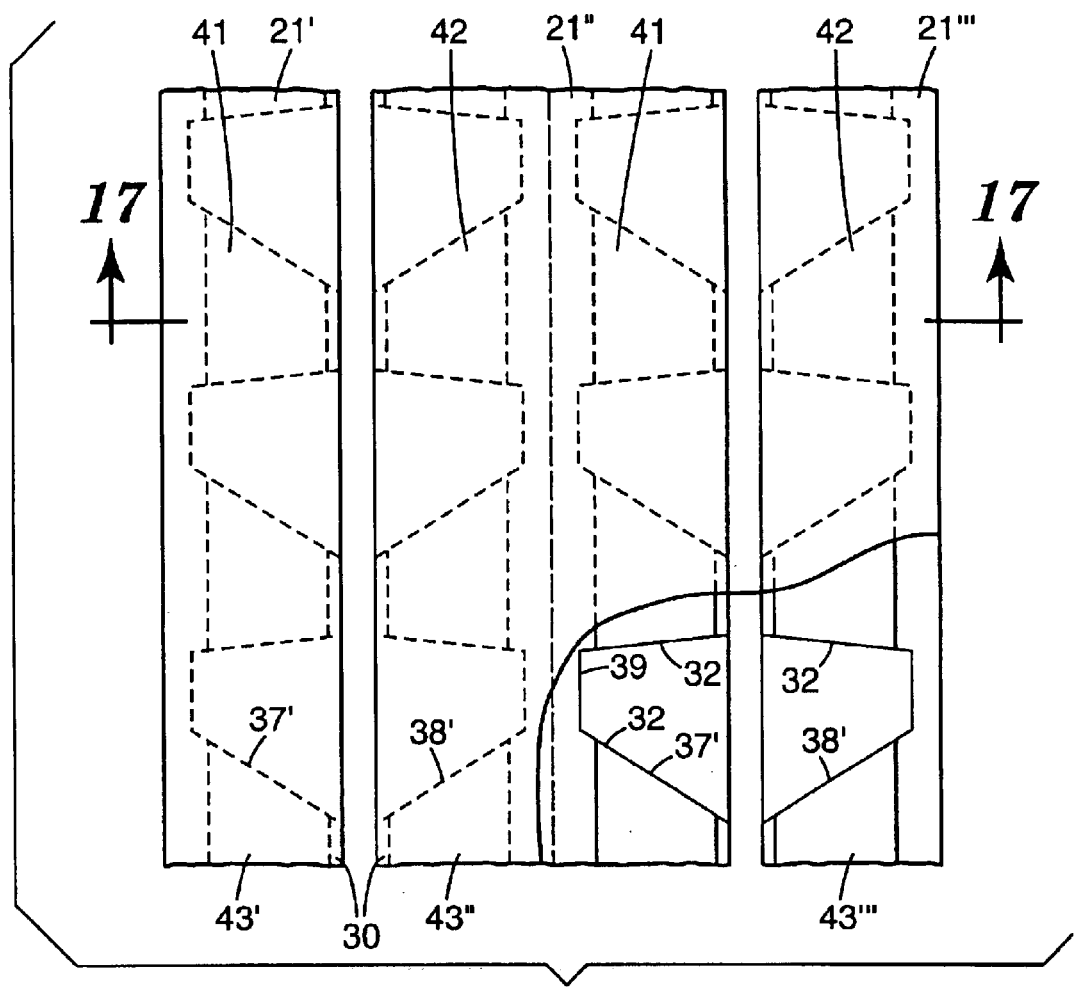
FIG. 16 is a top view of the FIG. 12 third dimensionally stable laminate further cut into a set of smaller third dimensionally laminates containing matched sets of tabs for use on opposite sides of a disposable garment.
Figure 17:
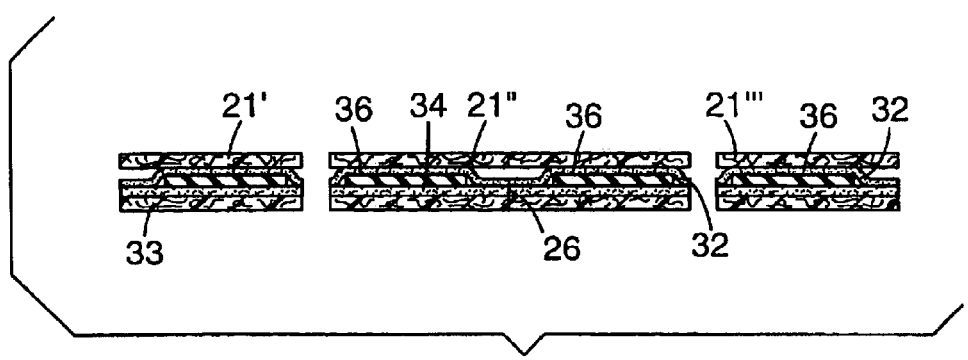
FIG. 17 is an end view of FIG. 16.

FIG. 16 is a top view of the FIG. 12 third dimensionally stable laminate further cut into a set of smaller third dimensionally laminates containing matched sets of ear portions 41 and 43 for use on opposite sides of a disposable garment as per FIG. 14. However, in FIG. 16, the ear portions are on opposite sides and reversed. Also in FIG. 16 end laminates 43' and 43''' each contain only one set of ear portions such that these two laminates would need to be paired or matched to provide a complete set of closure ear portions.

Figure 18:
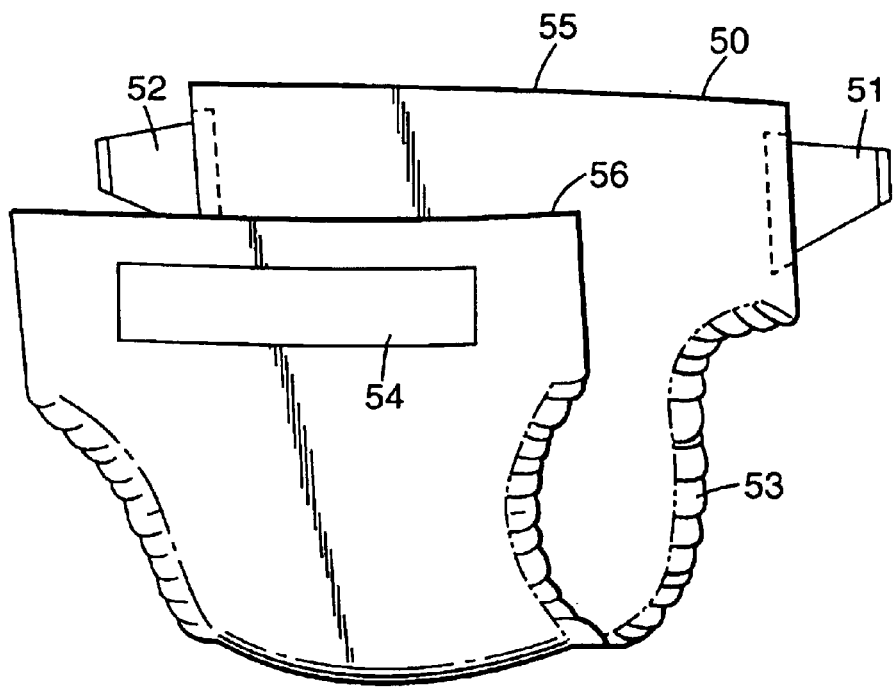
FIG. 18 is a disposable garment with a matched set of ear portions cut from the second or third dimensionally stable laminates.
Figure 19:
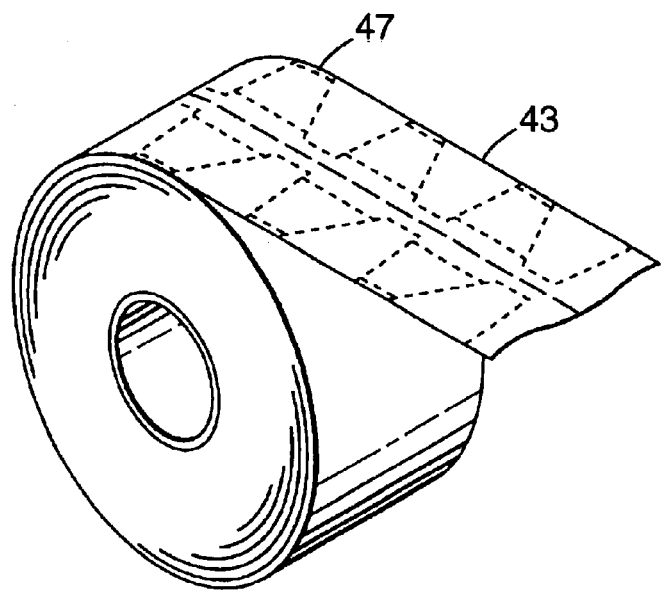
FIG. 19 is a roll containing a continuous length of the second or third dimensionally stable laminate.

FIG. 18 shows a disposable garment with a matched set of ear portions cut from either the second or third dimensionally stable laminates.

FIG. 19 is a roll containing a continuous length of the second or third dimensionally stable laminate such as the laminates 44 or 43" of FIG. 14 or 16.

Figure 20:
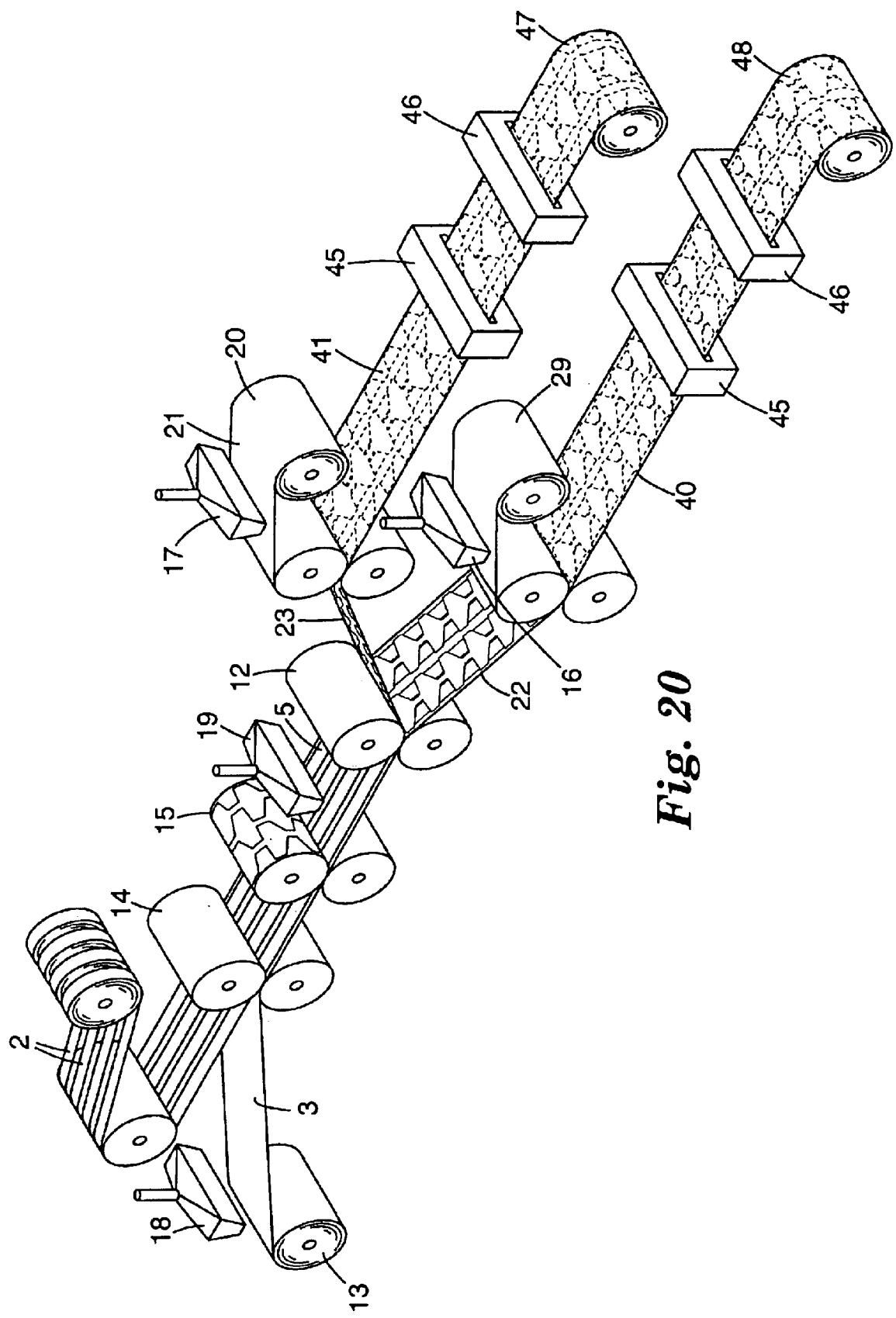
FIG. 20 is a perspective view of an apparatus and method according to a second embodiment of the present invention.

FIG. 20 is a perspective view of an apparatus and method according to a second embodiment of the present invention. In this embodiment, the process is as described relative to the FIG. 1 embodiment, however, the adhesive layer 6 is provided after the cutout station 15. This prevents adhesive build-up on the cutting elements.

I claim:

1. A process for forming profiled elastic laminates suitable for forming profiled elastic ear portions comprising:
   (a) providing a continuous length of at least one elastic web material having a first face and a second face and having a first width and a continuous length of a first extensible nonelastic web having a second width;
   (b) laminating the first face of the at least one elastic web material to the first extensible nonelastic web to form a first laminate;
   (c) continuously cutting the first laminate elastic web material into at least two adjacent continuous lengths of at least two nested profiled laminates which nested profiled laminates each have at least one profiled edge including the elastic web material and where adjacent profiled edges of adjacent profiled laminates are substantial negatives of each other;
   (d) separating the at least two adjacent profiled laminates;
   (e) providing a continuous length of at least one second nonelastic web having a third width;
   (f) laminating the at least one second nonelastic web to the elastic web material second face of the at least one profiled laminate such that the elastic web material is laminated between the first and second nonelastic webs forming at least one second dimensionally stable continuous laminate; and
   (g) collecting the second continuous laminate.

2. The process of claim 1 further comprising laminating a fastener element to the first laminate.

3. The process of claim 2 wherein the fastener element is a continuous length of mechanical fastener material.

4. The process of claim 1 further comprising laminating a fastener element to the first elastic web material.

5. The process of claim 1 further comprising laminating a fastener element to the second laminate.

6. The process of claim 1 wherein the elastic web material is a film elastic material.

7. The process of claim 1 wherein the elastic web material is a nonwoven elastic material.

8. The process of claim 1 wherein the first nonelastic web is a web of nonelastic fibers.

9. The process of claim 8 wherein the first nonelastic web is a nonwoven web.

10. The process of claim 9 wherein the first nonelastic web has an initial tensile yield force of at least 100 g/mm and an extensibility of at least 50 percent.

11. The process of claim 9 wherein the second nonelastic web is a web of nonelastic fibers.

12. The process of claim 9 wherein the second nonelastic web is a film web.

13. The process of claim 9 wherein the at least one profiled laminate is adhesively bonded to the second nonelastic web.

14. The process of claim 9 wherein the at least one profiled laminate is thermally bonded to the second nonelastic web.

15. The process of claim 1 wherein the first nonelastic web is a film web.

16. The process of claim 1 wherein the elastic web material is adhesively bonded to the first nonelastic web.

17. The process of claim 1 wherein the elastic web material is thermally bonded to the first nonelastic web.

18. The process of claim 17 wherein at least one nested profiled laminate has two profiled side edges each being a mirror image of the other suitable for forming opposing elastic elements on a disposable garment.

19. The process of claim 17 wherein multiple profiled laminates are joined to a single second nonelastic web.

20. The process of claim 19 wherein the second nonelastic web is a nonwoven web.

21. The process of claim 1 wherein the elastic web material is extrusion bonded to the first nonelastic web.

22. The process of claim 1 wherein the first laminate is cut into at least two nested lengths of profiled laminate such that there is no excess laminate material between the adjacent nested profiled laminates.

23. The process of claim 1 further comprising slitting the second continuous laminate.

24. The process of claim 1 wherein the second continuous laminate is collected in a roll form.

25. The process of claim 1 wherein discrete fastener elements are laminated to the profiled elastic containing portions of the second continuous laminate.

26. The process of claim 1 wherein a portion of the second laminate containing the profiled elastic laminate is selectively stretched to activate the elastic web.

27. The process of claim 1 wherein there is one continuous elastic web material and the first width is substantially equal to the second width.

* * * * *

UNITED STATES PATENT AND TRADEMARK OFFICE
CERTIFICATE OF CORRECTION

PATENT NO. : 6,780,272 B2  Page 1 of 1
DATED : August 24, 2004
INVENTOR(S) : Wood, Leigh E.

It is certified that error appears in the above-identified patent and that said Letters Patent is hereby corrected as shown below:

<u>Column 4,</u>
Line 61, please delete "direction oriented" and insert -- direction-oriented --.

Signed and Sealed this

First Day of February, 2005

JON W. DUDAS
*Director of the United States Patent and Trademark Office*